United States Patent [19]

Koseki et al.

[11] Patent Number: 5,374,744
[45] Date of Patent: Dec. 20, 1994

[54] METHOD FOR MANUFACTURING 4-SUBSTITUTED-γ-LACTONE AND NOVEL SUBSTANCE

[75] Inventors: Koshi Koseki; Hiroshi Kawakami; Takashi Ebata; Hajime Matsushita, all of Yokohama; Mikio Ono, Hamura, all of Japan

[73] Assignees: Japan Tobacco Inc.; Fuji Flavor Co., Ltd., Tokyo, Japan

[21] Appl. No.: 937,848

[22] PCT Filed: Feb. 17, 1992

[86] PCT No.: PCT/JP92/00150

§ 371 Date: Oct. 21, 1992

§ 102(e) Date: Oct. 21, 1992

[87] PCT Pub. No.: WO92/14720

PCT Pub. Date: Mar. 9, 1992

[30] Foreign Application Priority Data

Feb. 21, 1991 [JP] Japan ................. 3-077376

[51] Int. Cl.⁵ .................................. C07D 307/28
[52] U.S. Cl. ................................. 549/295; 549/314
[58] Field of Search ....................... 549/295, 314

[56] References Cited

PUBLICATIONS

Farbond et al. CA 113(22):197669f 1990.
M. Midland et al. (1980) *Tetrahedron Letters* 21:3549–3552.
Nishida, Yoshihiro et al., Agric. Biol. Chem., 51(3), pp. 635–640, 1987.
Senda, Shuji et al., Agric. Biol. Chem., 47(11), pp. 2595–2598, 1983.
Doolittle, R. E. et al., J. Chem. Ecol., 6, pp. 473–485, 1979.
Levene, P. A. et al., J. Biol. Chem., vol. 102, No. 1, pp. 187–201, 1933.
Chattopadhyay, S. et al., Synthetic Communications, 20(9), pp. 1299–1303, 1990.
Fukusaki, Eiichiro et al., Tetrahedron vol. 47, No. 32, pp. 6223–6230, 1991.
Leal, W. S., Naturwissenschaften 78, pp. 521–523, 1991.
Sugai, Takeshi et al. Synthesis pp. 1112–1114, Sep. 1990.
Nemoto Hideo et al., Heterocycles, vol. 31 No. 2, 1990.
Fukusaki, Eiichiro et al., Biosci. Biotech. Biochem., 56(7), pp. 1160–1161, 1992.
Ebata, Takashi et al., Biosci. Biotech. Biochem., 56(5), pp. 818–819, 1992.
Novel Lactone of Octanoic Acid Japanese 56-120678 Sep. 1981 Abstract.
The Merck Index (1983) Tenth Edition, Rahway, N.J., p. 987, entry 6758.

*Primary Examiner*—C. Warren Ivy
*Assistant Examiner*—A. A. Owens
*Attorney, Agent, or Firm*—Birch, Stewart, Kolasch & Birch

[57] ABSTRACT

An alkynyl group having a triple bond at the carbon atom at the 1-position is introduced to a carbon atom at the 1-position of 2,3-O-isopropylidene-D-ribofuranose. The diol part is then cleaved to obtain a lactol compound. This lactol compound is oxidized to obtain a lactone compound. The ketal part of the lactone compound is hydrolyzed and the compound is further subjected to a reduction reaction. The hydroxyl groups at the 2- and 3-positions are then eliminated, and the double bond between the 2- and 3-positions of the resultant compound is reduced to obtain a 4-substituted-γ-lactone.

21 Claims, No Drawings

METHOD FOR MANUFACTURING 4-SUBSTITUTED-γ-LACTONE AND NOVEL SUBSTANCE

TECHNICAL FIELD

The present invention relates to a method of manufacturing a 4-substituted-γ-lactone and a novel substance as a useful intermediate product thereof. The 4-substituted-γ-lactone include sex pheromones of vermin. More specifically, examples are (R,Z)-5-tetradecene-4-olide known as the sex pheromone of mamekogane (common name: Japanese beetle, scientific name: *Popillia japonica*) [J. H. Tumlinson et al, Science, 789, 197 (1977)] and (R,Z)-5-dodecene-4-olide known as the sex pheromone of a cupreous chafer. Therefore, the present invention is suitable in the verminous extermination of the mamekogane and the cupreous chafer in accordance with a pheromone trap (catching and killing by attraction).

BACKGROUND ART

The mamekogane and the cupreous chafer are vermin on fruit trees such as grape trees, and lawns. In recent years, damage to lawn by the mamekogane and the cupreous chafers in golf courses poses a serious problem.

Conventionally, these mamekogane and cupreous chafers are exterminated by pesticide applications. However, since a large amount of pesticide is used, the environmental pollution caused by contamination with pesticides in the vicinity of a golf course is a serious problem.

On the other hand, catching and killing by attraction using the sex pheromone of a vermin has an advantage in that a large number of vermin can be exterminated with a small amount of pheromone. This method is applied to some vermin in practice. Therefore, catching and killing by attraction of the mamekogane and cupreous chafers is assumed to be an extremely effective means to solve the above problem.

The following methods are known as methods of synthesizing the pheromone of the mamekogane, i.e., (R,Z)-5-tetradecene-4-olide (18).

1) A method in which, as indicated by reaction formula (I) below, (4R,5S,6S)-5,6-dihydroxytetradecane-4-olide (40) as an optically active intermediate is derived from arabinose, an intermediate (41) is then derived from the intermediate (40), and diols at the 5- and 6-positions of the intermediate (41) are eliminated to obtain a compound (18) [Y. Nishida, M. Konno, H. Hori, H. Ohrui, H. Meguro, Agric. Biol. Chem., 51, 635 (1987)]:

Reaction Formula (I)

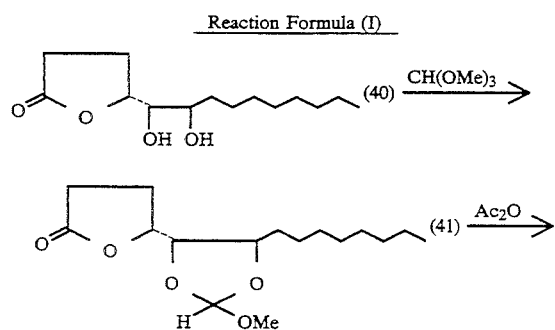

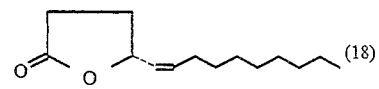

(wherein $R_1$ represents $C_8H_{17}$).

2) A method in which, as indicated by reaction formula (II) below, an acetylenic ketoester (52) synthesized from a 1-decyne derivative (51) is asymmetrically reduced (53) in the presence of (2S,3R)-(+)-4-dimethylamino-1,2-diphenyl-3-methyl-2-butanol [Chirald available from Aldrich Chemical Co., Inc.] and LiAlH$_4$, and the reduction product is subjected to fractional crystallization as an (R)-(+)-α-naphthylethylamine salt, thereby obtaining a compound (18) having high optical purity [S. Senda and K. Mori, Agric. Biol. Chem., 47, 2595 (1983)].

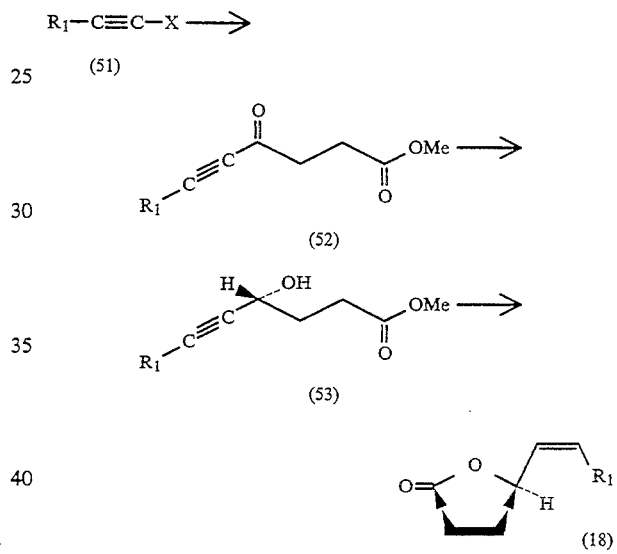

(wherein $R_1$ represents $C_8H_{17}$)

3) A method in which, as indicated by reaction formula (III), a compound (18) is obtained from (R)-glutamic acid, through butyrolactone, by using a Wittig reaction [R. E. Doolitle, et al, J. Chem. Ecol., 6, 473 (1980)].

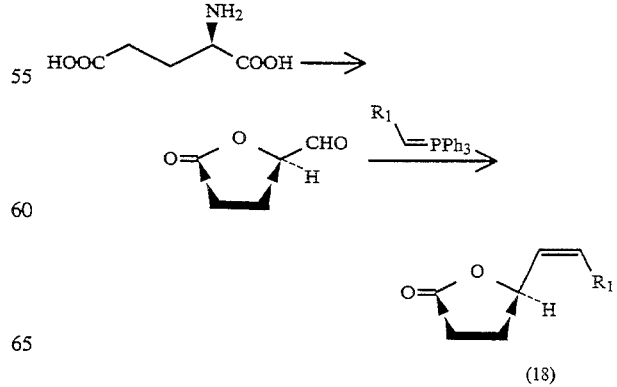

(wherein $R_1$ represents $C_8H_{17}$)

The conventional methods of manufacturing the compound (18) described above pose the following problems. Thus, in the method (1), a total of 12 steps are required from arabinose as the starting material, and the yield of the final compound (18) against arabinose is very low.

In the method (2), (2S,3R)-(+)-4-dimethylamino-1,2-diphenyl-3-methyl-2-butanol and (R)-(+)-α-naphthylethylamine which are required to obtain the optically active compound (18) are very expensive reagents, resulting in high manufacturing costs. In addition, in order to finally obtain the compound (18) having high optical purity, the (R)-(+)-α-naphthylethylamine salt must be subjected to fractional crystallization, thus complicating the process.

In the method (3), when nitric acid is reacted with (R)-glutamic acid to close the lactone ring, tetrahydro-5-oxy-2-furanonecarboxylic acid which is partially racemized is obtained. The racemic product must be purified to (R)-(−)-tetrahydro-5-oxy-2-furanonecarboxylic acid having high optical purity. In the final step, a cumbersome Wittig reaction for purification must be performed. For this reason, purification is cumbersome and the process is complicated.

For descriptive convenience, the method of synthesizing (R,Z)-5-tetradecene-4-olide (18) as the pheromone of the mamekogane is exemplified. The same problems as described above are also posed by a method of synthesizing (R,Z)-5-dodecene-4-olide (28) as the pheromone of the cupreous chafer represented by formula (28).

(28)

(wherein R₂ represents C₆H₁₃)

The present invention has been made in consideration of the above problems, and has as its object to provide a method of manufacturing a 4-substituted-γ-lactone and a novel substance as an intermediate product thereof, which includes neither an optical purity step nor a practically difficult step, and can manufacture the target compound by a short process, and is suitable for mass production.

DISCLOSURE OF INVENTION

According to the present invention, there is provided a method of manufacturing a 4-substituted γ-lactone represented by formula (8)

(8)

(wherein R represents an alkyl group having 4 to 14 carbon atoms), characterized by comprising the steps of:

(A) introducing an alknyl group having a triple bond at the 1-position thereof and 6 to 16 carbon atoms at the carbon atom at the 1-position of compound (1) represented by formula (1), thereby obtaining a compound (2) represented by formula (2)

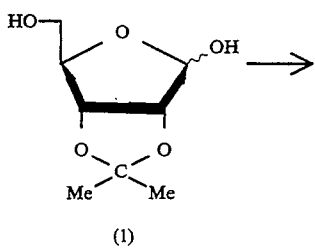
(1)

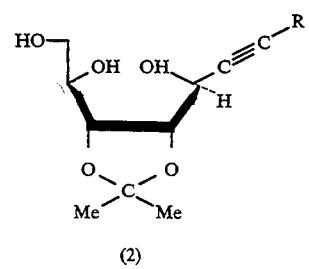
(2)

(wherein R represents the same as described above), (B) performing oxidation cleavage of the 1,2-diol part of the compound (2) obtained in step (A) to obtain a compound (3) represented by formula (3)

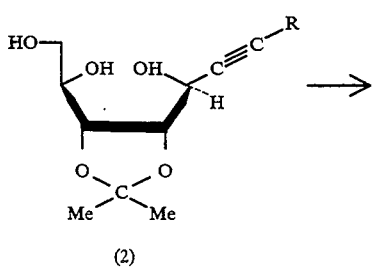
(2)

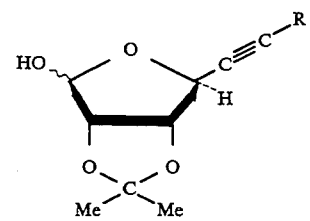
(3)

(wherein R represents the same as described above);

(C) oxidizing the compound (3) obtained in step (B) to obtain a compound (4) represented by formula (4)

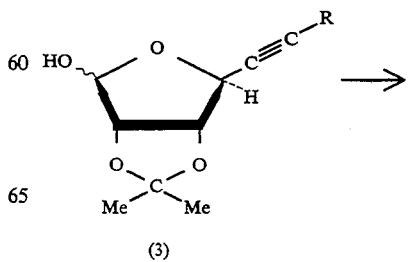
(3)

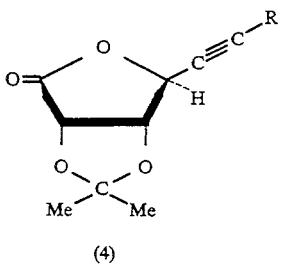

(4)

(wherein R represents the same as described above);

(D) treating the compound (4) obtained in step (C) with an acid to hydrolyze the ketal part of the compound (4) to obtain a compound (5) represented by formula (5)

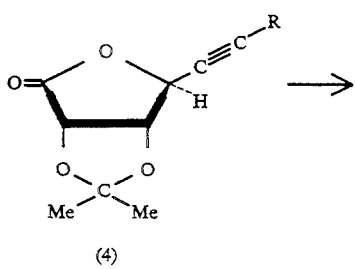

(4)

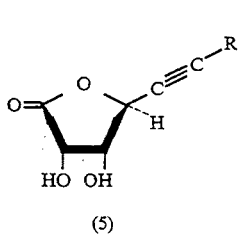

(5)

(wherein R represents the same as described above);

(E) subjecting the compound (5) obtained in step (D) to a reduction reaction and an elimination reaction of hydroxyl groups at the 2- and 3-positions to obtain a compound (7) represented by formula (7)

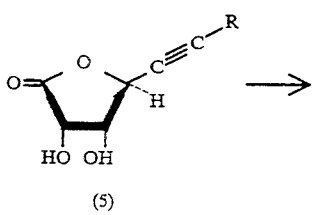

(5)

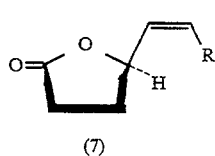

(7)

(wherein R represents the same content as described above); and (F) reducing the double bond between the 2- and 3-positions of the compound (7) obtained in step (E) to obtain a compound (8) represented by formula (8)

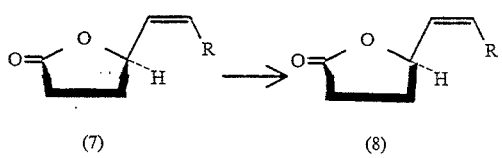

(7)   (8)

(wherein R represents the same as described above).

There is also provided a novel substance represented by formula (5) below:

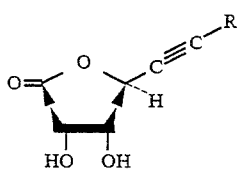

(5)

(wherein R represents an alkyl group having 4 to 14 carbon atoms).

There is further provided a novel substance represented by formula (7) below:

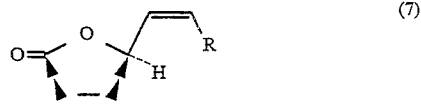

(7)

(wherein R represents an alkyl group having 4 to 14 carbon atoms).

The method of manufacturing a 4-substituted-γ-lactone according to the present invention will be described in detail below.

The compound (1) as the starting material is obtained by condensing a 2,3-diol of D-ribose with acetone to convert a ketal [Acetone Derivatives of D-Ribose, P. A. Levene and E. T. Stiller, J. Biol. Chem 102, PP. 187–201 (1933)]. Since D-ribose is easily accessible and inexpensive, it is one of the advantages of the present invention that D-ribose is the starting material of the present invention.

In step (A), the reaction for obtaining the compound (2) by introducing an alkynyl group having a triple bond at the 1-position thereof and 6 to 16 carbon atoms to the 1-position of the compound (1) is exemplified such that a Grignard reagent X—Mg—C≡C—R (X represents a halogen atom and R represents an alkyl group having 4 to 14 carbon atoms) having the alkynyl group is reacted with the compound (1). The solvent used in the reaction of step (A) is not particularly limited to a specific one. Examples of the solvent are tetrahydrofuran, diethyl ether, dioxane, and benzene.

The introduction means of the alknyl group having a triple bond at its 1-position and 6 to 16 carbon atoms to the 1-position of the compound is not limited to the use of the Grignard reagent. An acetylide Y—C≡C—R (Y represents Na, Li, K, Cu, Ca, or the like, and R represents an alkyl group having 4 to 14 carbon atoms) of each of various metals can be used.

Examples of the alkynyl group having a triple bond at its 1-position and 6 to 16 carbon atoms are a 1-decinyl group and a 1-octinyl group.

In step (B), the reaction for performing oxidation cleavage of the 1,2-diol part of the compound (2) to obtain the compound (3) is performed by causing the compound (2) to react with an aqueous sodium periodide solution. The solvent used in the reaction of step (B) is not particularly limited to a specific one. Examples include, ether, tetrahydrofuran, methanol, ethanol, petroleum ether, or the like.

Chromic acid, zinc tetraacerate, or the like can be used in place of sodium periodide as an oxidizing agent.

In step (C), the reaction for oxidizing the hydroxyl group at the 1-position of the compound (3) to obtain the compound (4) is not particularly limited to a specific one if it is a normal oxidation reaction. For example, the compound (3) is reacted with acetic anhydride in dimethylsulfoxide anhydride. The oxidizing agent used in this reaction is exemplified by silver carbonate, silver oxide, or the like.

In step (D), the reaction for obtaining the compound (5) by oxidizing the compound (4) to hydrolyze the ketal part at the 2- and 3-positions with an acidic treatment can be performed by acidic treatment using, e.g., 90% trifluoroacetic acid. The acidic treatment can be performed using hydrochloric acid, perhydrochloric acid, paratoluenesulfonic acid, or the like in place of trifluoroacetic acid.

In step (E), the step of obtaining the compound (7) by performing the reduction reaction and the elimination reaction of the hydroxyl groups at the 2- and 3-positions can be exemplified as follows. The triple bond between the carbon atoms at the 5- and 6-positions of the compound (5) is reduced to obtain a compound (6) represented by formula (6), and the hydroxyl groups at the 2- and 3-positions of the compound (6) are eliminated:

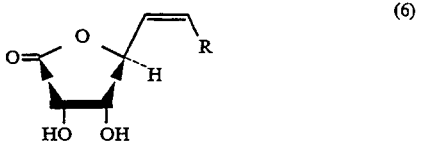

(wherein R represents an alkyl group having 4 to 14 carbon atoms).

First, the step of obtaining the compound (6) by reducing the triple bond between the carbon atoms at the 5- and 6-positions of the compound (5) can be performed by normal catalytic reduction. More specifically, after the compound (5) is dissolved in a proper solvent, the solution is stirred in a hydrogen atmosphere in the presence of a Lindlar catalyst, Raney-nickel, platinum, palladium carbonate, or the like. The solvent is not particularly limited to a specific one. An alcohol solvent such as ethanol or methanol is generally used.

This reduction reaction can also be performed by reduction using diimine or diisobutylaluminum hydroxide in place of catalytic reduction.

The reaction for obtaining the compound (7) by eliminating the hydroxyl groups at the 2- and 3-positions of the compound (6) can be performed in accordance with a method disclosed in Agric. Biol. Chem., 51,635–640 (1987) as represented by scheme (IV) below. More specifically, the compound (6) is reacted with orthoformate (60) to obtain an orthoester derivative (61). The orthoester is eliminated from the orthoester derivative to obtain the compound (7). The orthoformate (60) is not particularly limited to a specific one, but trimethyl orthoformate or triethyl orthoformate can be appropriately used. The elimination reaction of the orthoester derivative (61) can be performed by a reaction with acetic anhydride.

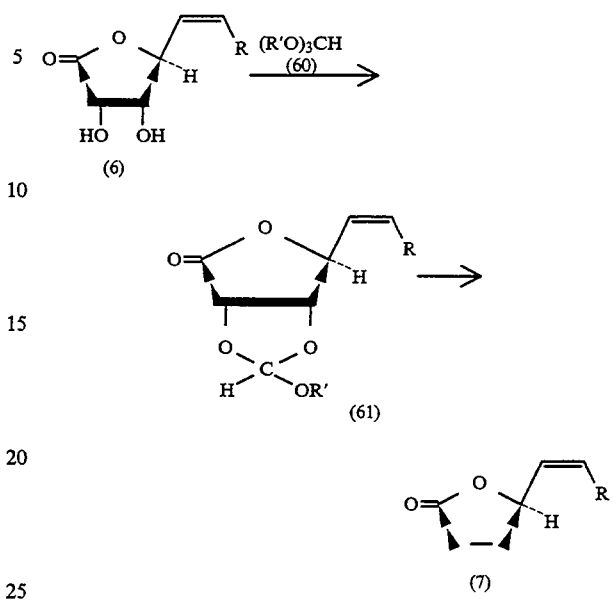

(wherein R is an alkynyl group having a triple bond at its 1-position and 6 to 16 carbon atoms, and R' represents $C_2H_5$ or $CH_3$).

However, the reaction of the hydroxyl groups at the 2- and 3-positions of the compound (6) is not limited to the above reaction. Any reaction can be employed if the hydroxyl groups at the 2- and 3-positions are eliminated to obtain the compound (7). For example, a method of obtaining cyclic thiocarbonate (E. J. Corey, R. A. E. Winter, J. Am. Chem. Soc., 87, 934 (1965)) is available as a method used in the above reaction.

The compound (7) may also be derived from the compound (5) in an order opposite to the above step. More specifically, first, the hydroxyl groups at the 2- and 3-positions of the compound (5) are eliminated to obtain a compound (6') represented by formula (6'). Thereafter, the triple bond between the carbon atoms at the 5- and 6-positions of the compound (6') is then reduced to obtain a double bond, thereby obtaining the compound (7).

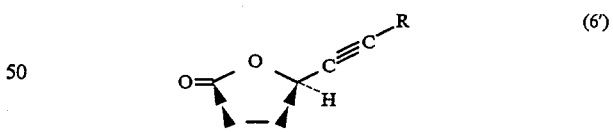

(wherein R represents an alkyl group having 4 to 14 carbon atoms).

In step (F), the reaction of obtaining the compound (8) by reducing the double bond between the 2- and 3-positions of the compound (7) can be performed in accordance with, e.g., a method proposed by B. H. Lipshutz et al. (SYNLETT, PP. 64–66, September 1989). More specifically, the compound (7) is added in a tetrahydrofuran solution containing copper iodide and lithium chloride, and chlorotrimethylsilane is added thereto. Thereafter, the resultant solution is reacted by adding n-$Bu_3SnH$ thereto, thereby obtaining the compound (8).

The compound (8) can also be obtained by a method of reducing the compound (7) using phenylsilane in the presence of Mo(CO)$_6$ or Pd(PPh$_3$)$_4$ in chloroform, or a method reducing the compound (7) by Fe(CO)$_6$ in an aqueous sodium hydroxide solution.

The reduction reaction can be performed by the normal contact reduction described above with reference to step (E). However, a reduction method using the method proposed by B. H. Lipshutz et al., as described above, can provide the compound (8) in a higher yield.

According to the method of manufacturing a 4-substituted-γ-lactone and a novel substance of the present invention, D-ribose as an easily accessible, inexpensive material is used as the starting material, the number of steps is relatively small, and reactions easy to perform in practice are used. Therefore, the manufacturing cost can be advantageously reduced, and a 4-substituted-γ-lactone having high optical purity can be easily manufactured.

The 4-substituted-γ-lactone represented by formula (8) is generally known as an insect pheromone. More specifically, the 4-substituted-γ-lactone can be exemplified by (R,Z)-5-tetradecene-4-olide (R=C$_8$H$_{17}$) as the pheromone of the mamekogane and (R,Z)-5-dodecene-4-olide (R=C$_6$H$_{13}$) as the pheromone of the cupreous chafer. According to the method of the present invention, these 4-substituted-γ-lactone can be easily manufactured with high optical purity. As a result, the industrial applicability of these compounds to catching and killing by attraction can be enhanced.

BEST MODE OF CARRYING OUT THE INVENTION

The present invention will be described in detail by way of its examples below.

EXAMPLE 1

Manufacture of (R,Z)-5-Tetradecene-4-Olide (18) [R=C$_8$H$_{17}$ in Formula (8) above]

Step a

Synthesis of 2,3-O-isopropylidene-D-ribofuranose: Compound (1)

20 g of D-ribose as a starting material were reacted with 400 ml of acetone to obtain 14 g of a compound (1) in accordance with the method described in J. Biol. Chem. 102, PP. 187–201 (1933). The physical data of the product coincided with reference values.

Step b

Synthesis of (2R,3R,4R,5R)-2,5-dihydroxy-3,4-isopropylidenedioxypentadeca-6-yne-1-ol: Compound (12)

240 ml of a 0.99M tetrahydrofuran solution of ethylmagnesium bromide (EtMgBr) were added to a solution of 52 ml of 1-decyne and 50 ml of anhydrous tetrahydrofuran in a nitrogen flow within the temperature range of 25° C. to 30° C. for about an hour. After the resultant solution was stirred at room temperature for an hour, a solution obtained by dissolving 15 g (78.9 mmol) of the compound (1) obtained in step a in 50 ml of tetrahydrofuran was cooled to the solution temperature range of 5° C. to 10° C. with ice and water. The cooled solution was dropped into the above stirred solution, and the mixture was stirred at 5° C. for 2 hours. This mixture was poured in a saturated aqueous ammonium chloride solution, and the reaction solution was extracted with ether three times. The extracted solution was sequentially washed with water and brine solution and was dried with magnesium sulfate anhydride. Thereafter, the solvent and 1-decyne in the extracted solution were distilled to obtain 15.7 g of a compound (12) as a viscous oily substance (yield: 70.9%). The physical data of the compound (12) were as follows:

$n_D$ 1.4754, 22.5° C. $[\alpha]_D$ −36.6° (c 1.955, CHCl$_3$, 22° C.) IR $v_{max}$, cm$^{-1}$3366 (s), 2988 (m), 2930 (s), 2860 (s), 1222 (s), 1075 (s) $^1$H-NMR $\delta$ppm $^{CDCl_3}$; 0.82 (3H, t, J=6.0 Hz), 1.20–1.40 (10H), 1.36 (3H, s), 1.42 (3H, s), 1.49 (2H, m), 2.24 (2H, dt, J=1.9, 7.0 Hz), 3.68 (1H, dd, J=5.9, 11.2 Hz), 3.85 (1H, dd, J=3.4, 11.2 Hz), 3.92 (1H, ddd, J=3.4, 5.9, 9.2 Hz), 4.13 (1H, dd, J=5.3, 8.0 Hz), 4.19 (1H, dd, J=5.3, 8.0 Hz), 4.57 (1H, td, J=1.7, 8.1 Hz)

Step c

Synthesis of (3S,4R,5R)-5-(1-decynyl)-2-hydroxy-3,4-isopropylidenedioxytetrahydrofuran: Compound (13)

15.7 g (47.8 mmol) of the compound (12) obtained in step b were dissolved in 50 ml of ether and were strongly stirred with 200 ml of a 10 wt % aqueous sodium periodide solution at room temperature. After two hours, the stirred solution was extracted with ether three times, and the extracted solution was sequentially washed with water and brine solution. The washed extracted solution was dried with magnesium sulfate anhydride. Thereafter, the solvent in the extracted solution was distilled at a reduced pressure to obtain 2.46 g of a compound (13) as a viscous oily substance (yield: 88%). The physical data of the resultant compound (13) were as follows:

Calculated Values; C$_{17}$H$_{28}$O$_4$ C:68.89%, H:9.52%
Measured Values; C:68.6%, H:9.7% $n_D$ 1.4686, 22.5° C. $[\alpha]_D$ −4.0° (c 1.487, CHCl$_3$, 22.5° C.) IR $v_{max}$, cm$^{-1}$; 3340 (s), 2926 (s), 2860 (s), 1071 (s), 1035 (s) $^1$H-NMR $\delta$ppm $^{CDCl_3}$; 0.88 (3H, t, J=6.6 Hz), 1.2–1.4 (12H), 1.4–1.55 (2H, m), 2.17 (2H, m)

The measured values of two different isomers separated on the NMR will be described below.

Isomer 13a) 1.32, 1.46 (3H, s), 4.74, 4.89 (1H, d, J=5.8 Hz), 4.66 (1H, br, s), 5.43 (1H, s)

Isomer 13b) 1.35, 1.53 (3H, s), 4.59 (1H, dd, J=3.5, 7.0 Hz), 4.66 (1H, br, s), 4.73 (1H, brd, J=7.0 Hz), 5.32 (1H, d, J=3.5 Hz)

Step d

Synthesis of (2S,3S,4R)-2,3-isopropylidenedioxy-5-tetradecy-4-olide: Compound (14)

13.27 g (44.8 mmol) of the compound (13) obtained in step c were dissolved in 40 ml of anhydrous dimethylsulfoxide, 40 ml of acetic anhydride were added thereto, and the resultant solution was stirred overnight at room temperature. 300 ml of water were added to the stirred solution, and this aqueous solution was extracted with ether three times. This extracted solution was washed with water and saline solution, and was dried with anhydrous magnesium sulfate. Then, the solvent of the extracted solution was distilled at a reduced pressure to obtain 20 g of a compound (14) as a viscous oily substance. This oily substance was purified by silica gel chromatograph (silica gel: 300 g; developing solution: hexane and ethyl acetate) to obtain 7.35 g of the pure compound (14) in a yield of 65%. The physical data of the resultant compound (14) were as follows:

Calculated Values; C$_{17}$H$_{26}$O$_4$ C:69.36%, H:8.90%
Measured Values; C:69.3%, H:8.7% $n_D$ 1.4660, 22.7° C. $[\alpha]_D$ +19.5° (c 1.85, CHCl$_3$, 22.7° C.) IR $v_{max}$, cm$^{-1}$ 2994, 2932, 1798, 1752, 1226, 1164, 1151, 1100 (s) $^1$H-NMR $\delta$ppm $^{CDCl_3}$; 0.88 (3H, t, J=7.0 Hz), 1.2–1.4

(10H), 1.45–1.55 (2H, m), 1.39, 1.46 (3H, s), 2.21 (2H, dt, J=2.2, 7.2 Hz), 4.75 (1H, dd, J=0.4, 5.2 Hz), 4.86 (1H, d, J=5.2 Hz), 5.14 (1H, td, J=0.4, 1.7 Hz)

Step e

Synthesis of (2S,3S,4R)-2,3-dihydroxy-5-tetradecyn-4-olide: Compound (15)

200 ml of 90 wt% trifluoroacetic acid were added to 6.87 g (23.3 mmol) of the compound (14) obtained in step d, and the resultant solution was stirred at room temperature for 15 minutes. After the solvent was distilled at a reduced pressure, ether was added to the residue. This solution was stirred with an aqueous sodium bicarbonate solution, and the water layer was removed, thereby eliminating the residual acidic substance. The remaining ether layer was sequentially washed with water and brine solution and was dried with magnesium sulfate anhydride. Thereafter, the solvent in the ether layer was distilled at a reduced pressure to obtain 5.47 g of a brown solid product (yield:92%). The solid product was recrystallized using 130 ml of a hexane/isopropyl ether solution mixture obtained by mixing hexane and isopropyl ether at a mixing ratio of 75:55, thereby obtaining 4.84 g of a colorless fibrous compound (15) (yield:89%). The physical data of the resultant compound (15) were as follows:

Calculated values; $C_{14}H_{22}O_4$ C:66.12%, H:8.72%
Measured Values; C:66.0%, H:8.7% m.p. 97.5°–98.0° C. $[\alpha]_D$ −63.4° (c 1.03, CHCl$_3$, 22° C.) IR $\upsilon_{max}$, cm$^{-1}$; 3450, 3250 (brs), 2928, 2860, 1760 (s), 1185, 1152, 1011, 934 (s) $^1$H-NMR $\delta$ppm $^{CDCl_3}$; 0.89 (3H, t, J=6.3 Hz), 1.2–1.4 (10H), 1.50 (2H, m), 2.22 (2H, dt, J=2.1, 7.0 Hz), 4.45 (1H, d, J=4.5 Hz), 4.69 (1H, d, J=4.5 Hz), 5.08 (1H, t, J=2.1Hz)

Step f

Synthesis of (2S,3S,4S,5Z)-2,3-dihydroxy-5-tetradecen-4-olide: Compound (16)

1.924 g (7.58 mmol) of the compound (15) obtained in step e were dissolved in 20 ml of ethanol, 40 mg of 5 wt % Pd—CaCO$_3$/Pb (Lindlar catalyst) were added thereto, and the resultant solution was strongly stirred in a hydrogen flow. The solid product in the reaction solution was filtered, and the solvent was distilled at a reduced pressure, thereby obtaining a colorless solid product. This solid product was recrystallized using 50 ml of a hexane/isopropyl ether solution mixture obtained by mixing hexane with isopropyl ether at a mixing ratio of 20:30 to obtain 1.45 g of a colorless fibrous compound (16) (yield:74.6%). The physical data of the resultant compound (16) were as follows.

Calculated values; $C_{14}H_{22}O_4$ C:65.60%, H:9.44%
Measured Values; C:65.4%, H:9.5% m.p. 73.0°–73.5° C. $[\alpha]_D$ −90.4° (c 0.979, CHCl$_3$, 23° C.) IR $\upsilon_{max}$ KBr, cm$^{-1}$ 3420, 3300 (brs), 2958, 2928, 2856 (s), 1660 (w), 1756 (s), 1466, 1431 (w), 1185, 1156, 922 (s) $^1$H-NMR $\delta$ppm $^{CDCl_3}$; 0.88 (3H, t, J=7.0 Hz), 1.20–1.50 (12H), 2.1–2.25 (2H, m), 4.22 (1H, d, J=4.7 Hz), 4.53 (1H, d, J=4.7 Hz), 5.23 (1H, d, J=9.2 Hz), 5.31 (1H, dddd, J=10.4, 9.0, 1.4, 1.4 Hz), 5.75 (1H, ddd, J=7.8, 7.8, 10.4 Hz)

Step g

Synthesis of (2S,3S,4S,5Z)-2,3-methoxymethylidenedioxy-5-tetradecen-4-olide: Compound (101) [R=C$_8$H$_{17}$ in compound (61) above]

598 mg (2.33 mmol) of the compound (16) obtained in step f were dissolved in 10 ml of trimethyl orthoformate, 2 μl of concentrated sulfuric acid were added thereto, and the resultant solution was stirred at room temperature for 15 minutes. 30 ml of ether were added to this reaction solution, and the solution was extracted. This extracted solution was subsequently washed with an aqueous sodium bicarbonate solution and brine solution and was dried with magnesium sulfate anhydride. The solvent in the extracted solution was distilled at a reduced pressure to obtain 770 mg of a compound (101) as a colorless oily product. The physical data of the as the resultant compound (101) were as follows:

Calculated Values; $C_{16}H_{26}O_5$ C:64.41%, H:8.78%
Measured Values; C:64.0%, H:9.0% n$_D$ 1.4666, 24° C. $[\alpha]_D$ −81.4° (c 0,950, CHCl$_3$, 24° C.) IR $\upsilon_{max}$, cm$^{-1}$; 2926, 2858 (s), 1787 (s), 1660 (w), 1195, 1123, 1077 (s), 984, 977 (s) $^1$H-NMR $\delta$ppm $^{CDCl_3}$; 0.88 (3H, t, J=7.0 Hz), 1.20–1.50 (12H), 2.15–2.25 (2H, m)

The measured values of two different isomers separated on the NMR will be described below.

Isomer 101a) 3.32 (3H, s), 4.52 (1H, dd, J=0.85, 6.5 Hz), 4.84 (1H, d, J=6.5 Hz), 5.31 (1H, d, J=10.7 Hz), 5.41 (1H, brd, J=9.2 Hz), 5.77 (1H, dddd, J=1.0, 7.5, 7.5, 10.7 Hz), 5.90 (1H, brs)

Isomer 101b) 3.36 (3H, s), 4.67 (1H, d, J=5.5 Hz), 4.92 (1H, d, J=5.5 Hz), 5.25–5.34 (3H), 5.91 (1H, brs)

Step h

Synthesis of (4S,5Z)-tetradeca-2,5-dien-4-olide: Compound (17)

In an argon atmosphere, 21 ml of acetic anhydride and 864 μl of acetic acid were added to 1.23 g (480 mmol) of the compound (101) obtained in step f, and the resultant mixture was heated to 140° C. and reacted for 5 hours. The solvent of the reaction solution was distilled at a reduced pressure to obtain 1.21 g of a compound (17) as a yellow oily substance. The physical data of the resultant compound (17) were as follows:

IR $\upsilon_{max}$, cm$^{-1}$; 2926 (s), 2860 (s), 1794 (s), 1760 (S), 1480 (m), 1156, 1094, 1019 (s), 818 (s) $^1$H-NMR $\delta$ppm $^{CDCl_3}$; 0.89 (3H, t, J=6.5 Hz), 1.25–1.50 (12H), 2.1–2.35 (2H, m), 5.14 (1H, tt, J=1.6, 9.1 Hz), 5.8 (2H, m), 6.14 (1H, dd, J=2.0, 5.6 Hz), 7.33 (1H, dd, J=1.6, 5.6 Hz)

Step i

Synthesis of (R,Z)-5-tetradecen-4-olide: Compound (18)

In an argon atmosphere, 10 ml of anhydrous tetrahydrofuran were added to 570 mg (3.0 mmol) of purified copper iodide (CuI) and 318 mg (7.5 mmol) of lithium chloride (LiCl) dried at a reduced pressure and 130° C., and the resultant solution was stirred at room temperature for about 30 minutes. The resultant transparent solution was cooled to about −60° C., a solution obtained by dissolving 336 mg (1.511 mmol) of the compound (17) obtained in step h in 3.5 ml of tetrahydrofuran was added to the above transparent solution, and 0.81 ml (6 mmol) of chlorotrimethylsilane chloride immediate after distillation were added to the above solution. The resultant mixture was stirred for 10 minutes, and 1.5 ml (5.5 mmol) of distilled and purified n-Bu$_3$SnH were added thereto in a small amount each time over 5 minutes. Thereafter, cooling was stopped, and the temperature of the reaction solution was raised to 0° C. at room temperature over about 30 minutes. 20 ml of a 10% aqueous potassium fluoride solution were added to this reaction solution, and the mixture was stirred. The produced precipitate was filtered. This filtrate was extracted with tetrahydrofuran and concentrated, 30 ml of a 10% aqueous potassium fluoride solution were added to the residue, and the solution was stirred for 15 minutes. 30 ml of ether were further added to the above solution, and the resultant solution was stirred for 15 minutes. The stirred solution was filtered, the filtrate was separated, and the water layer thereof was extracted with ether. The extracted solution was collected and sequentially washed with water and brine solution and was dried with anhydrous magnesium sulfate. Then, the crude product obtained by concentrating the extracted solution was purified by chromatography using silica gel (270–400 meshes, 10 g, developing solution of hexane: ethyl acetate at a mixing ratio of 98:2 to 96:4), thereby obtaining 265 mg of a compound (18) (yield:78%). The IR and NMR spectra of the resultant compound (18) coincided with the reported data [References: Y. Nishida, et al, Agric. Biol. Chem., 51, 635 (1987) (to be referred to as reference 1 hereinafter) and R. E. Dolitle, et al, J. Chem. Ecol., 6, 473 (1980) (to be referred to as reference 2 hereinafter)]. Other physical data were as follows.

Calculated values; $C_{14}H_{24}O_2$ C:74.95%, H:10.78% Measured Values; C:74.8%, H:10.9% $n_D$ 1.4666, 22° C. $[\alpha]_D$ −71.0° (c 5.387, $CHCl_3$, 26° C.)

| Reported reference value | Reference 1) | −70.4° |
|---|---|---|
| | c = 0.4 | |
| | Reference 2) | −70.0° |
| | c = 5.0 | |

EXAMPLE 2

Step d-2

1 g of a Fetizon reagent ($Ag_2CO_3$/Celite) prepared in accordance with a method proposed by v. Balogh et al. (V. Balogh, M. Fetizon, M. Golfier, J. Org. Chem., 36, 1339) was added to 15 ml of benzene, and about 10 ml of benzene were distilled from the resultant solution to obtain an anhydrous condition. 91 mg (0.31 mmol) of the compound (13) obtained in step c of Example 1 were added to the above solution, and the mixture was heated and refluxed for 8.5 hours. The resultant solid product was filtered, and the solvent was distilled at a reduced pressure to obtain 85 mg of a compound (14) as an oily substance (yield:94%). The physical data of the compound (14) coincided with those of the compound (14) obtained in step d of Example 1. A compound (18) as in Example 1 was obtained following the same procedures as in steps e to i of Example 1.

EXAMPLE 3

100 mg of the compound (7) obtained in step h of Example 1 were dissolved in 1.5 ml of ethanol, 5 mg of 1% Pd—C were added thereto, and the resultant solution was stirred for 1.5 hours under cooling with ice in a hydrogen atmosphere. Thereafter, the Pd—C was filtered off, and the filtrate was concentrated. The concentrate was fractionated by a high-performance liquid chromatograph (silica gel; YMC, A-014, 6×300 mm, elute; isopropyl ether: hexane (2:1); stream speed 3 ml/min, detection by a differential refractometer), thereby obtaining 8 mg of a compound (18) eluted in a retention time of 20 to 22 minutes. The physical data of the compound (18) coincided with those of the compound obtained in step h of Example 1.

EXAMPLE 4

Manufacture of (R,Z)-5-dodecen-4-olide [R=$C_{16}H_{13}$ in Formula (8) above]

Step b'

Synthesis of (2R,3R,4R,5R)-2,5-dihydroxy-3,4-isopropylidenedioxy-trideca-6-yne-1-ol: Compound (22)

32 ml (24.2 g, 220 mmol) of 1-octyne and 50 ml of tetrahydrofuran were added to 100 ml (200 mmol) of an ether solution of hexylmagnesium bromide (2N—Hex—MgBr) in an argon atmosphere over 25 minutes under cooling with ice. The resultant mixture was stirred for one hour and 20 minutes after the temperature was raised to 40° to 50° C. A solution obtained by dissolving 10.0 g (52.7 mmol) of the compound (1) synthesized following the same procedures as in step a of Example 1 in 30 ml of tetrahydrofuran was dropped in the above mixture over 20 minutes under cooling with ice. The organic layer of the solution obtained by stirring the above mixture at room temperature for an hour was separated, and the water layer was extracted with chloroform three times. All of the resultant organic layers were combined, the combined organic layers were sequentially washed with water and brine solution, and dried with anhydrous magnesium sulfate. The solvent and the remaining 1-octyne were distilled at a reduced pressure to obtain 15.6 g (52.0 mmol) of a compound (22) as a viscous oily substance (yield:99%).

The physical data of the resultant compound (2) were as follows:

$n_D$ 1.4568, 23.9° C. $[\alpha]_D$ −36.0° (c 1.00, $CHCl_3$, 27° C.) IR $\nu_{max}$, $cm^{-1}$ 3338 (s), 2980 (m), 2934 (s), 2864 (s), 2238 (s), 1222 (s), 1073 (s)

Step c'

Synthesis of (3S,4R,5R)-5-(1-octynyl)-2-hydroxy-3,4-isopropylidenedioxytetrahydrofuran: Compound (23)

15.3 g (51.0 mmol) of the compound (22) obtained in step b' were dissolved in 50 ml of ether, and the resultant solution was strongly stirred with 200 ml of a 10 wt % aqueous sodium periodide solution at room temperature. After two hours, the organic layer was separated, and the water layer was extracted with ether three times. Then, the combined organic layers were sequentially washed with water and brine solution, and were dried with anhydrous magnesium sulfate. Thereafter, the solvent was distilled at a reduced pressure to obtain 10.6 g (39.6 mmol) of a compound (23) as a viscous substance (yield:78%). The physical data of the resultant compound (23) were as follows:

$n_D$ 1.7062, 22.4° C. $[\alpha]_D$ −5.9° (c 1.00, $CHCl_3$, 25° C.) IR $\nu_{max}$,$cm^{-1}$; 3416 (S), 2936 (S), 2864 (S), 2230 (w), 1073 (s), 1035 (s)

Step d'

Synthesis of (2S,3S,4R)-2,3-isopropylidenedioxy-5-dodecyn-4-olide: Compound (24)

1.00 g (3.74 mmol) of the compound (23) obtained in step c' was dissolved in 10 ml of methylene chloride, 4.21 g of molecular sieve (MS-4A) and 4.21 g (11.2 mmol) of pyridinium dichromate (PDC) were added thereto, and the resultant solution was stirred for 5 hours. Thereafter, 100 ml of methylene chloride were added to the above solution, and the mixture was filtered with florisil (60–100 meshes). The resultant filtrate was sequentially washed with a saturated aqueous copper sulfate solution, water, and brine solution, and was dried with anhydrous magnesium sulfate. The solvent was distilled at a reduced pressure to obtain 590 mg (2.22 mmol) of a compound (24) as a viscous substance (yield:59%). The physical data of the resultant compound (24) were as follows:

Calculated values; $C_{15}H_{22}O_4$ C:67.64%, H:8.33% Measured Values; C:67.66%, H:8.36% $n_D$ 1.7062, 21.9° C. $[\alpha]_D$ +14.6° (c 1.00, CHCl$_3$, 25° C.) IR $v_{max}$, cm$^{-1}$; 2990 (m), 2936 (s), 2240 (w), 1798 (s), 1224 (m), 1164 (s), 1151 (s), 1100 (s) $^1$H-NMR $\delta$ppm $^{CDCl_3}$; 0.90 (3H, t, J=7.0 Hz), 1.2–1.6 [14H, m, including 1.40 (3H, s) and 1.47 (3H, s)], 2.22 (2H, dt, J=2.0, 7.1 Hz), 4.75 (1H, d, J=5.2 Hz), 4.86 (1H, d, J=5.2 Hz), 5.15 (1H, t, J=2.0 Hz)

Step e'

Synthesis of (2S,3S,4R)-2,3-dihydroxy-5-dodecyn-4-olide: Compound (25)

20 ml of 90 wt % trifluoroacetic acid were added to 590 mg (2.22 mmmol) of the compound (24) obtained in step d', and the resultant mixture was stirred at room temperature for 20 minutes. The solvent was distilled at a reduced pressure, ether was added to the residue, the resultant solution was stirred with an aqueous sodium bicarbonate solution, and the remaining acidic substances were eliminated by leaving off the water layer. The remaining ether layer was then sequentially washed with water and brine solution and was dried with anhydrous magnesium sulfate. Thereafter, the solvent in the ether layer was distilled at a reduced pressure to obtain 464 mg of an opaline solid product. This solid product was recrystallized using a dichloromethane/hexane solution mixture to obtain 381 mg (1.69 mmol) of a white fibrous compound (25) (yield:76%). The physical data of the resultant compound (25) were as follows:

Calculated Values; $C_{12}H_{18}O_4$ C:63.70%, H:8.02% Measured Values; C:63.27%, H:7.89% m.p. 103.0°–104.0° C. $[\alpha]_D$ −68.2° (c 1.07, CHCl$_3$, 25° C.)

IR $v_{max}$, cm$^{-1}$ 3426 (br), 3300 (br), 2930 (m), 2864 (m), 2240 (w), 1760 (s), 1185 (s), 1152 (m), 1011 (m) 932 (m) $^1$H-NMR $\delta$ppm $^{CDCl_3}$; 0.89 (3H, t, J=6.9 Hz), 1.20–1.60 (8H, m), 2.22 (2H, dt, J=2.0, 7.0 Hz), 2.89 (1H, brs), 2.96 (1H, brs), 4.46 (1H, d, J=4.6 Hz), 4.69 (1H, d, J=4.6 Hz), 5.09 (1H, t, J=2.0 Hz)

Step f'

Synthesis of (2S,3S,4S,5Z)-2,3-dihydroxy-5-dodecen-4-olide: Compound (26)

1.02 g (4.51 mmol) of the compound (25) obtained in step e' were dissolved in 20 ml of ethanol, 40 mg of 5 wt % Pd—CaCO$_3$/Pb (Lindlar catalyst) were added thereto, and the resultant solution was strongly stirred in a hydrogen atmosphere. The solid product in the reaction solution was filtered with Celite, and the solvent was distilled at a reduced pressure, thereby obtaining a white crystal. This crystal was recrystallized from a dichloromethane/hexane solution mixture to obtain 967 mg (4.24 mmol) of a white fibrous compound (26) (yield:94%). The physical data of the resultant compound (26) were as follows:

Calculated Values; $C_{12}H_{20}O_4$ C:63.13%, H:8.83% Measured Values; C:62.97%, H:8.60% m.p. 72.0°–73.0° C. $[\alpha]_D$ −90.4° (c 1.00, CHCl$_3$, 24° C.) IR $v_{max}$ KBr, cm$^{-1}$ 3440 (br), 3314 (br), 2956 (s), 2922 (s), 2856 (s), 1777 (s), 1763 (s), 1653 (w), 1466 (w), 1437 (w), 1187 (s), 1156 (s), 926 (s) $^1$H-NMR $\delta$ppm $^{CDCl_3}$; 0.89 (3H, t, J=6.9 Hz), 1.20–1.50 (8H, m), 2.05–2.25 (2H, m), 2.87 (1H, brs), 3.13 (1H, brs), 4.23 (1H, d, J=4.7 Hz), 4.52 (1H, d, J=4.7 Hz), 5.20–5.40 (2H, m), 5.70–5.85 (1H, m)

Step g'

Synthesis of (2S,3S,4S,5Z)-2,3-methoxymethylidene-dioxy-5-dodecen-4-olide: Compound (201) [R=C$_6$H$_{13}$ in Compound (16) above]

641 mg (2.81 mmol) of the compound (26) obtained in step f' were dissolved in 10 ml of trimethyl orthoformate, 2 μl of concentrated sulfuric acid were added thereto, and the resultant solution was stirred at room temperature for 15 minutes. 10 ml of ether were added to this reaction solution, and the solution as extracted. This extracted solution was sequentially washed with an aqueous sodium bicarbonate solution and brine solution and was then dried with anhydrous magnesium sulfate. The solvent in this extracted solution was distilled at a reduced pressure to obtain 760 mg (quantitatively) of a compound (201) as a colorless oily substance. The physical data of the resultant compound (201) were as follows:

IR $v_{max}$, cm$^{-1}$ 2960 (s), 2932 (s), 2860 (s), 1792 (s), 1659 (w), 1466 (m), 1193 (s), 1123 (s)

Step h'

Synthesis of (4S,5Z)-dodeca-2,5-dien-4-olide: Compound (27)

25 ml of acetic anhydride and 1 ml of acetic acid were added to 1.50 g of the compound (201) obtained in step f' in an argon atmosphere, and the resultant solution was heated to 140° C. and reacted for 6 hours. The solvent of the reaction solution was distilled at a reduced pressure to obtain 1.16 g (quantitatively) of a compound (27) as a light yellow oily substance. The physical data of the resultant compound (27) were as follows:

IR $v_{max}$, cm$^{-1}$: 2928 (s), 2860 (s), 1794 (s), 1760 (s), 1466 (w), 1158 (s), 1094 (m), 1025 (m), 818 (m) $^1$H-NMR $\delta$ppm $^{CDCl_3}$; 0.89 (3H, t, J=6.9 Hz), 1.20–1.50 (8H, m), 2.05–2.35 (2H, m), 5.14 (1H, tt, J=1.5, 9.1 Hz), 5.71–5.85 (2H, m), 6.14 (1H, dd, J=2.0, 5.6 Hz), 7.32 (1H, dd, J=1.5, 5.6 Hz)

Step i'

Synthesis of (R,Z)-5-dodecen-4-olide: Compound (28)

In an argon atmosphere, 40 ml of anhydrous tetrahydrofuran were added to 1.95 g (10.2 mmol) of copper (LiCl) iodide (CuI) and 1.09 g (25.7 mmol) of lithium chloride dried at a reduced pressure and 130° C., and the resultant solution was stirred at room temperature for about 15 minutes. The resultant transparent solution was cooled to about −60° C., and a solution obtained by dissolving 1.16 g of the compound (27) obtained in step h' in 21 ml of tetrahydrofuran was added to the above cooled solution. Subsequently, 2.72 ml (20.4 mmol) of chlorotrimethylsilane (TMSCl) were added to the resultant solution, this solution mixture was stirred for 10 minutes, and 5.04 ml (16.0 mmol) of distilled and purified n-Bu$_3$SnH were added to stirred solution mixture in a small amount each time over about 5 minutes. Cooling was then stopped, and the temperature of the reaction solution was raised to 0° C. at room temperature over about 30 minutes. 60 ml of a 10% aqueous potassium fluoride (KF) solution were added to the above reaction solution, the mixture was stirred, and the produced precipitate was filtered. The organic layer was separated from this filtrate, and the remaining water layer was extracted with 100 ml of ether three times. The extracted solution was concentrated, 90 ml of a 10% aqueous potassium fluoride solution were added to the resultant residue, and the solution mixture was stirred for 15 minutes. Ether was added to this solution and stirred for 15 minutes. The resultant solution was filtered, the filtrate was separated, and its water layer was extracted with 100 ml of ether three times. These organic layers were collected, sequentially washed with water and brine solution, and dried with anhydrous magnesium sulfate. The organic layers were concentrated to obtain a crude product, and the crude product was purified by a column chromatograph using a developing solvent (hexane: diethyl tether=91:9 to 83:17), thereby obtaining 875 mg (4.46 mmol) of a compound (28) as a colorless transparent oily substance (yield:74%). The physical data of the resultant compound (28) were as follows:

HRMS Calculated Value; $C_{12}H_{20}O_2$ 196.1463 Measured Value; 196.1466 Calculated Value; $C_{12}H_{20}O_2$ C:73.43% H:10.27% Measured Value; C:73.35% H:10.34% $n_D$ 1.4627, 24.8° C. $[\alpha]_D$ −79.5° (c 0.99, $CHCl_3$, 21° C.) IR $v_{max}$, cm$^{-1}$ 2930 (s), 2860 (m), 1781 (s), 1460 (m), 1180 (s), 1013 (m), 980 (m), 907 (m) $^1$H-NMR $\delta$ppm $^{CDCl_3}$; 0.88 (3H, t, J=6.7 Hz), 1.20–1.47 (8H, m), 1.95 (1H, dddd, J=8.2, 9.0, 9.1, 12.6 Hz), 2.11 (2H, m), 2.39 (1H, ddt, J=6.5, 12.1, 12.6 Hz), 5.25 (1H, dddd, J=0.9, 6.5, 8.3, 9.0 Hz), 5.46 (1H, ddt, J=1.5, 8.3, 10.8 Hz), 5.67 (1H, ddt, J=0.9, 7.6, 10.8 Hz); 2.56 (2H, m).

We claim:

1. A method of manufacturing a 4-substituted-γ-lactone represented by formula (8):

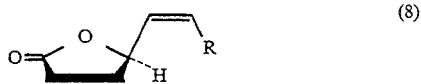

(8)

where R represents an alkyl group having 4 to 14 carbon atoms, comprising the steps of:

(A) introducing an alkynyl group having a triple bond at the 1-position thereof and 6 to 16 carbon atoms to the carbon atom at the 1-position of compound (1) represented by formula (1), thereby obtaining compound (2) represented by formula (2)

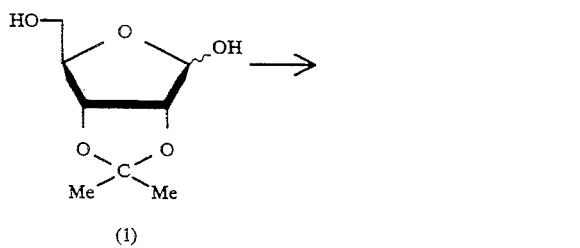

(1)

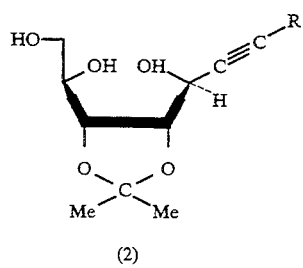

(2)

wherein R is the same as above;

(B) performing oxidation cleavage of the 1,2-diol part of compound (2) obtained in step (A) to obtain compound (3) represented by formula (3)

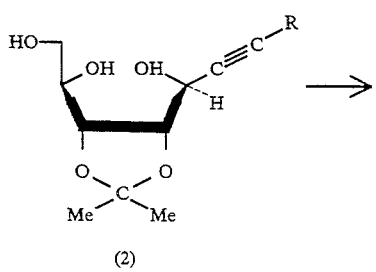

(2)

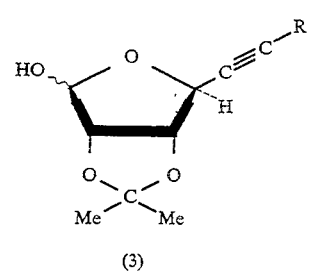

(3)

wherein R is the same as above;

(C) oxidizing compound (3) obtained in step (B) to obtain compound (4) represented by formula (4)

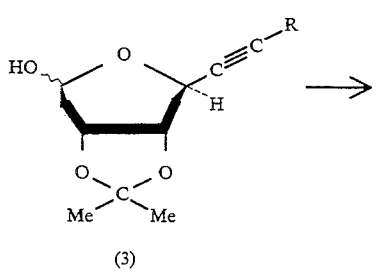

(3)

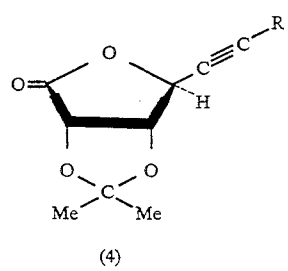

(4)

wherein R is the same as above;

(D) treating compound (4) obtained in step (C) with an acid to hydrolyze the ketal part of said compound (4) to obtain compound (5) represented by formula (5)

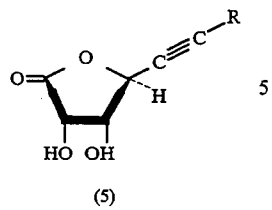

wherein R is the same as above;

(E) subjecting compound (5) obtained in step (D) to a reduction reaction and an elimination reaction of hydroxyl groups at the 2- and 3-positions to obtain compound (7) represented by formula (7)

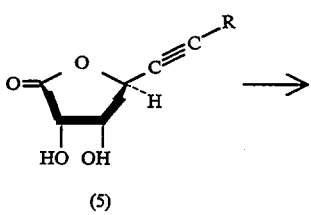

wherein R is the same as above; and (F) reducing the double bond between the 2- and 3-position of said compound (7) obtained in step (E) to obtain compound (8) represented by formula (8)

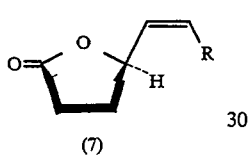

wherein R is the same as above.

2. The method of manufacturing a 4-substituted-γ-lactone according to claim 1, wherein in step (E), said compound (5) is subjected to said reduction reaction to obtain compound (6) represented by formula (6), and hydroxyl groups at the 2- and 3-positions of said compound (6) are eliminated to obtain compound (7):

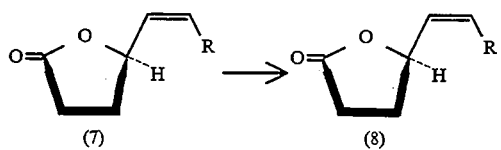

wherein R represents an alkyl group having 4 to 14 carbon atoms.

3. The method of manufacturing a 4-substituted-γ-lactone according to claim 1, wherein in step (E), said hydroxyl groups at the 2- and 3-positions of said compound (5) are eliminated to obtain compound (6') represented by formula (6'), and said compound (6') is subjected to said reduction reaction to obtain said compound (7):

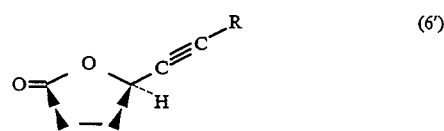

wherein R represents an alkyl group having 4 to 14 carbon atoms.

4. A compound represented by formula (5):

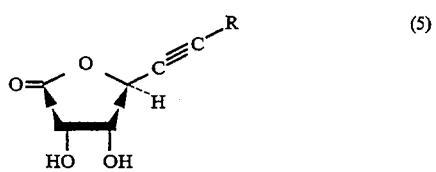

wherein R represents an alkyl group having 4 to 14 carbon atoms.

5. A method of manufacturing (R,Z)-5-tetradecen-4-olide represented by formula (18):

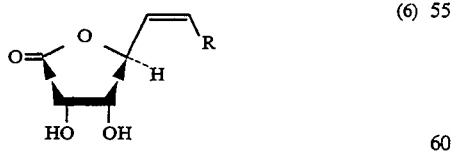

wherein $R_1$ represents $C_8H_{17}$, comprising the steps of:

(A) introducing a 1-decynyl group to the carbon atom at the 1-position of 2,3-O-isopropylidene-D-ribofuranose represented by formula (1) to obtain (2R,3R,4R,5R)-2,5-dihydroxy-3,4-isopropylidenedioxypentadeca-6-yn-1-ol represented by formula (12)

wherein $R_1$ is the same as above;

(B) performing oxidation cleavage of the 1,2-diol part of said (2R,3R,4R,5R)-2,5-dihydroxy-3,4-isopropylidenedioxypentadeca-6-yn-1-ol represented by formula (12) obtained in step (A) to obtain (3S,4R,5R)-5-(1-decynyl)-2-hydroxy-3,4-isopropylidenedioxytetrahydrofuran represented by formula (13)

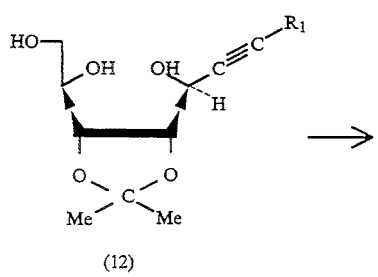

(12)

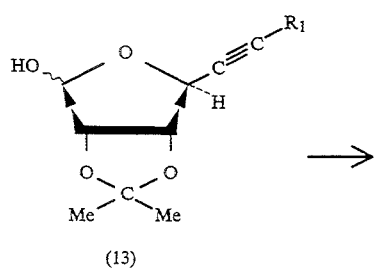

(13)

wherein $R_1$ is the same as above;

(C) oxidizing said (3S,4R,5R)-5-(1-decynyl)-2-hydroxy-3,4-isopropylidenedioxytetrahydrofuran represented by formula (13) obtained in step (B) to obtain (2S,3S,4R)-2,3-isopropylidenedioxy-5-tetradecyn-4-olide represented by formula (14)

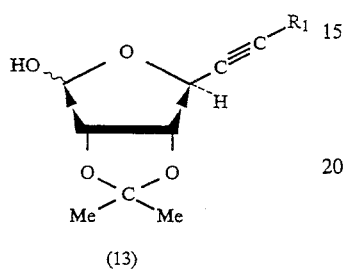

(13)

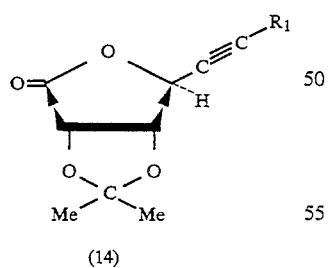

(14)

wherein $R_1$ is the same as above;

(D) treating said (2S,3S,4R)-2,3-isopropylideneodioxy-5-tetradecyn-4-olide represented by formula (14) obtained in step (C) with an acid to hydrolyze the ketal part of said compound (14), thereby obtaining (2S,3S,4R)-2,3-dihydroxy-5-tetradecyn-4-olide represented by formula (15)

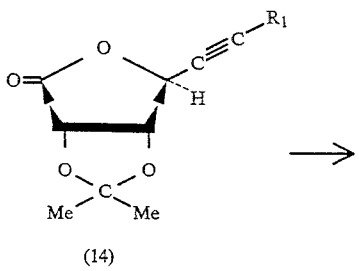

(14)

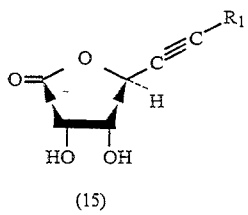

(15)

wherein $R_1$ is the same as above;

(E) subjecting said (2S,3S,4R)-2,3-dihydroxy-5-tetradecyn-4-olide represented by formula (15) obtained in step (D) to a reduction reaction and an elimination reaction of the hydroxyl groups at the 2- and 3-positions, thereby obtaining (4S,5Z)-tetradeca-2,5-dien-4-olide represented by formula (17)

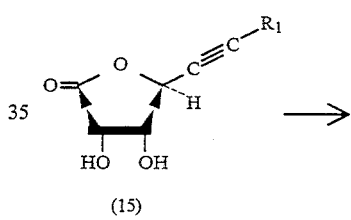

(15)

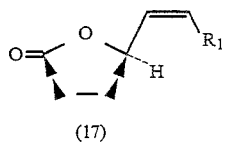

(17)

wherein $R_1$ is the same as above; and (F) reducing the double bond between the 2- and 3-positions of said (4S,5Z)-tetradeca-2,5-dien-4-olide represented by formula (17) obtained in step (E) to obtain (R,Z)-5-tetradecen-4-olide represented by formula (18)

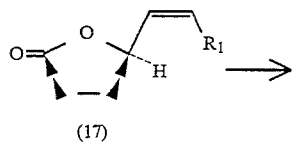

(17)

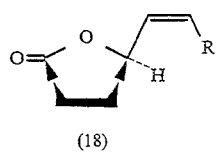

(18)

wherein $R_1$ is the same as above.

6. A method of manufacturing (R,Z)-5-dodecen-4-olide represented by formula (28):

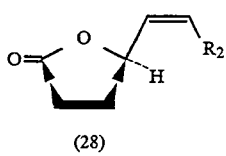

(28)

wherein $R_2$ represents $C_6H_{13}$, comprising the steps of:

(A) introducing a 1-octynyl group to the carbon atom at the 1-position of 2,3-O-isopropylidene-D-ribofuranose represented by formula (1) to obtain (2R,3R,4R,5R)-2,5-dihydroxy-3,4-isopropylidenedioxytrideca-6-yn-1-ol represented by formula (22)

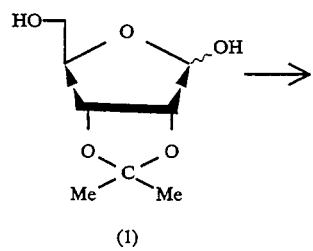

(1)

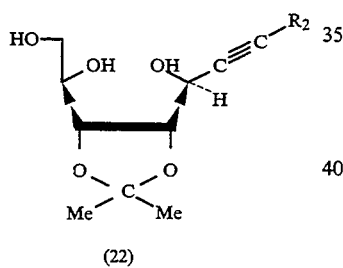

(22)

wherein $R_2$ is the same as above;

(B) performing oxidation cleavage of the 1,2-diol part of said (2R,3R,4R,5R)-2,5-dihydroxy-3,4-isopropylidenedioxytrideca-6-yn-1-ol represented by formula (22) obtained in step (A) to obtain (3S,4R,5R)-5-(1-octynyl)-2-hydroxy-3,4-isopropylidenedioxytetrahydrofuran represented by formula (23)

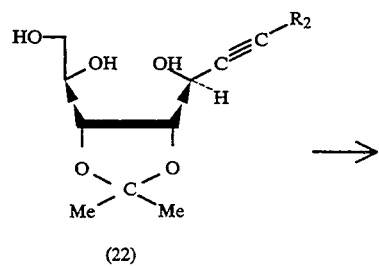

(22)

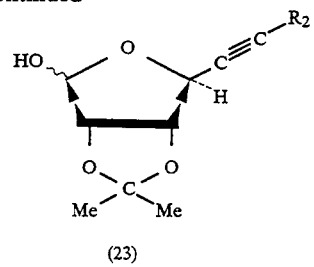

(23)

wherein $R_2$ is the same as above;

(C) oxidizing said (3S,4R,5R)-5-(1-octynyl)-2-hydroxy-3,4-isopropylidenedioxytetrahydrofuran represented by formula (23) obtained in step (B) to obtain (2S,3S,4R)-2,3-isopropylidenedioxy-5-dodecyn-4-olide represented by formula (24)

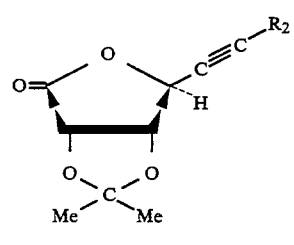

(23)

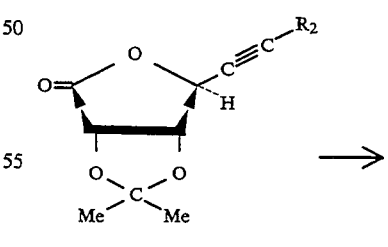

(24)

wherein $R_2$ is the same as above;

(D) treating said (2S,3S,4R)-2,3-isopropylidenedioxy-5-dodecyn-4-olide represented by formula (24) obtained in step (C) with an acid to hydrolyze the ketal part of said compound (24), thereby obtaining (2S,3S,4R)-2,3-dihydroxy-5-dodecyn-4-olide represented by formula (25)

(24)

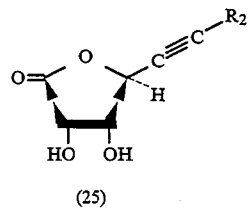

(25)

wherein $R_2$ is the same as above;

(E) subjecting said (2S,3S,4R)-2,3-dihydoxy-5-dodecyn-4-olide represented by formula (25) obtained in step (D) to a reduction reaction and an elimination reaction of the hydroxyl groups at the 2- and 3-positions, thereby obtaining (4S,5Z)-dodeca-2,5-dien-4-olide represented by formula (27)

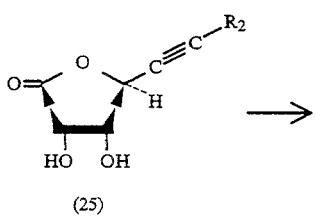

(25)

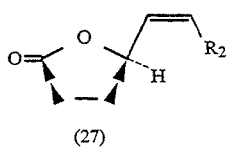

(27)

wherein $R_2$ is the same as above; and (F) reducing the double bond between the 2- and 3-positions of said (4S,5Z)-dodeca-2,5-dien-4-olide represented by formula (27) obtained in step (E) to obtain (R,Z)-5-dodecen-4-olide represented by formula (28)

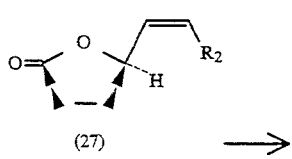

(27)

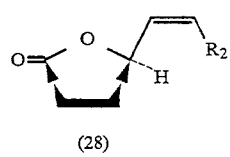

(28)

wherein $R_2$ is the same as above.

7. The method according to claim 1, wherein said introducing said alkynyl group at the 1-position of compound (1) is carried out by reacting a Grignard reagent having said alkynyl group with said compound (1).

8. The method according to claim 7, wherein a solvent is a member selected from the group consisting of tetrahydrofuran, diethyl ether, dioxane, and benzene.

9. The method according to claim 1, wherein said introducing said alkynyl group at the 1-position of compound (1) is carried out by employing an acetylide Y—C≡C—R, wherein Y is a member selected from the group consisting of Na, Li, K, Cu, and Ca, and R is an alkyl group having 4 to 14 carbon atoms.

10. The method according to claim 1, wherein said alkynyl group is a member selected from the group consisting of a 1-decinyl group and a 1-octinyl group.

11. The method according to claim 1, wherein said performing said oxidation cleavage of step (B) is carried out by reacting said compound (2) with an aqueous sodium periodide solution.

12. The method according to claim 11, wherein a solvent is a member selected form the group consisting of ether, tetrahydrofuran, methanol, ethanol, and petroleum ether.

13. The method according to claim 1, wherein said performing said oxidation cleavage of step (B) is carried out by employing a member selected from the group consisting of chromic acid and zinc tetraacetate.

14. The method according to claim 1, wherein said oxidizing of step (C) is carried out by reacting said compound (3) with a member selected from the group consisting of acetic anhydride in dimethylsulfoxide anhydride, silver carbonate, and silver oxide.

15. The method according to claim 1, wherein said acid of step (D) is a member selected from the group consisting of 90% trifluoroacetic acid, hydrochloric acid, perhydrochloric acid, and paratoluenesulfonic acid.

16. The method according to claim 1, wherein said reduction reaction of step (E) is carried out by a method selected from the group consisting of normal catalytic reduction, reduction using diimine, and reduction using diisobutylaluminum hydroxide.

17. The method according to claim 1, wherein said elimination reaction of step (E) is carried out by reacting said compound (6) with orthoformate to obtain an orthoester derivative, and subsequently eliminating said orthoester from said orthoester derivative by reacting said orthoester derivative with acetic anhydride to obtain said compound (7).

18. The method according to claim 17, wherein said orthoformate is a member selected from the group consisting of trimethyl orthoformate and triethyl orthoformate.

19. The method according to claim 1, wherein said reducing of step (F) is carried out by adding said compound (7) to a tetrahydrofuran solution containing copper iodide and lithium chloride, adding chlorotrimethylsilane thereto, and then reacting the resultant solution by adding n-Bu₃SnH thereto, thereby obtaining said compound (8).

20. The method according to claim 1, wherein said reducing of step (F) is carried out by employing phenylsilane in the presence of $Mo(CO)_6$ or $Pd(PPh_3)_4$ in chloroform, or by employing $Fe(CO)_6$ in an aqueous sodium hydroxide solution.

21. The method according to claim 1, wherein said reducing of step (F) is carried out by normal contact reduction.

* * * * *